(12) United States Patent
Barzilay et al.

(10) Patent No.: US 9,750,699 B2
(45) Date of Patent: Sep. 5, 2017

(54) BIOACTIVE COMPOUNDS PROTECTION METHOD AND COMPOSITIONS CONTAINING THE SAME

(71) Applicant: NUTRINIA LTD., Nazareth (IL)

(72) Inventors: Amir Barzilay, Zur Hadassah (IL); Hagit Koren-Lichtig, Moshav Mishmeret (IL)

(73) Assignee: NUTRINIA LTD., Nazareth (IL)

( * ) Notice: Subject to any disclaimer, the term of this patent is extended or adjusted under 35 U.S.C. 154(b) by 0 days.

(21) Appl. No.: 14/531,892

(22) Filed: Nov. 3, 2014

(65) Prior Publication Data

US 2015/0118280 A1    Apr. 30, 2015

Related U.S. Application Data

(62) Division of application No. 10/561,541, filed as application No. PCT/IL2004/000532 on Jun. 17, 2004, now Pat. No. 8,877,232.

(60) Provisional application No. 60/548,164, filed on Mar. 1, 2004, provisional application No. 60/479,860, filed on Jun. 20, 2003.

(51) Int. Cl.
| | |
|---|---|
| *A61K 9/19* | (2006.01) |
| *A61K 38/28* | (2006.01) |
| *A61K 47/36* | (2006.01) |
| *A23K 40/30* | (2016.01) |
| *A23K 20/147* | (2016.01) |
| *A23K 20/168* | (2016.01) |
| *A23K 50/60* | (2016.01) |
| *A23L 33/10* | (2016.01) |

(52) U.S. Cl.
CPC .............. *A61K 9/19* (2013.01); *A23K 20/147* (2016.05); *A23K 20/168* (2016.05); *A23K 40/30* (2016.05); *A23K 50/60* (2016.05); *A23L 33/10* (2016.08); *A61K 38/28* (2013.01); *A61K 47/36* (2013.01); *A23V 2002/00* (2013.01)

(58) Field of Classification Search
CPC .......... A23V 2002/00; A23V 2200/224; A23V 2200/328; A23V 2250/5114; A23K 20/147; A23K 20/168; A23K 40/30; A23K 50/60; A23L 33/10; A61K 38/28; A61K 47/36; A61K 9/19
See application file for complete search history.

(56) References Cited

U.S. PATENT DOCUMENTS

| | | | |
|---|---|---|---|
| 4,832,967 A | 5/1989 | Autant | |
| 5,013,569 A * | 5/1991 | Rubin | A23C 9/1528 426/585 |
| 5,279,832 A | 1/1994 | Greissinger | |
| 5,418,010 A | 5/1995 | Janda | |
| 5,531,989 A * | 7/1996 | Paul | A23J 3/08 424/130.1 |
| 5,545,410 A | 8/1996 | Fox | |
| 6,048,562 A * | 4/2000 | Mandralis | A61K 9/1658 264/4.1 |
| 6,482,517 B1 * | 11/2002 | Anderson | A01N 25/26 424/422 |
| 6,797,293 B2 | 9/2004 | Shin | |
| 6,989,195 B2 | 1/2006 | Anderson | |
| 2002/0064549 A1 | 5/2002 | Shehadeh | |
| 2002/0136809 A1 | 9/2002 | Shin | |
| 2003/0077297 A1 | 4/2003 | Chen | |
| 2003/0175403 A1 | 9/2003 | Gurin | |
| 2003/0190309 A1 | 10/2003 | Zink | |
| 2004/0121002 A1 | 6/2004 | Lee | |

FOREIGN PATENT DOCUMENTS

| | | |
|---|---|---|
| EP | 0631731 | 1/1995 |
| EP | 0495349 | 8/1995 |
| EP | 0750854 | 1/1997 |
| EP | 1393636 | 3/2004 |
| GB | 2345836 | 7/2000 |
| JP | 10-155428 | 6/1998 |
| JP | 11-009196 | 1/1999 |
| JP | 2000-050793 | 2/2000 |
| JP | 2000-116320 | 4/2000 |
| JP | 2002-209513 | 7/2002 |
| WO | 88/01506 | 3/1988 |
| WO | 93/12772 | 7/1993 |
| WO | 99/62558 | 12/1999 |
| WO | 02/058735 | 8/2002 |
| WO | 02/094224 | 11/2002 |
| WO | 03/013538 | 2/2003 |
| WO | 03/030865 | 4/2003 |
| WO | 03/077661 | 9/2003 |
| WO | 2004/003188 | 1/2004 |
| WO | 2005/115473 | 12/2005 |

(Continued)

OTHER PUBLICATIONS

Adachi et al., (2003) Preparation of a wate-in-oil-in-water (W/O/W) Type Microcapsules by a Single-droplet-drying Method and Change in Encapsulation Efficiency of a Hydrophiilic Substance during Storage. Bioscience, Biotechnology and Biochemistry 67(6): 1376-81.

Chantalau et al., (2008) Insulin, insulin analogues and diabetic retinopathy. Archives of Physiology and Biochemistry 114(1): 54-62

Hou et al., (1999) Applied studies of plant meridian system: I. The effect of agri-wave technology on yield and quality of tomato. Am J Chin Med 27(1): 1-10—abstract.

(Continued)

*Primary Examiner* — Snigdha Maewall
(74) *Attorney, Agent, or Firm* — Cooley LLP

(57) ABSTRACT

The present invention relates to means for protecting bioactive materials in mammalian food or feed formulations used to enhance the health status of mammals.

16 Claims, No Drawings

(56) References Cited

FOREIGN PATENT DOCUMENTS

WO    2009/086132    7/2009

OTHER PUBLICATIONS

Hudayberdiyev et al., (1997) Oral Multiple W/O/W Emulsion Formulation for Recombinant Human Insulin. Journal of Controlled Release 48: 346-7.

Lin Song-yi et al., (2001) Application of Microencapsulation Technology in Food Industry. Beverage & Fast Frozen Food Industry 7(3): 16-9 abstract.

Zhang Su-hua et al., (2003) Developmental Trend of Health Food. Culinary Science Journal of Yangzhou University 2003(2): 40-4 abstract.

Zylberberg and Pepper (2001) Continuous insulin infusion: promoting growth in low birth weight infants. Neonatal Network 20(1): 17-24.

* cited by examiner

US 9,750,699 B2

BIOACTIVE COMPOUNDS PROTECTION METHOD AND COMPOSITIONS CONTAINING THE SAME

CROSS-REFERENCE TO RELATED APPLICATIONS

This application is a divisional of U.S. patent application Ser. No. 10/561,541, filed Dec. 19, 2005, which is the U.S. National Stage of International Application No. PCT/IL2004/000532, filed Jun. 17, 2004, which claims the benefit of U.S. Provisional Application Nos. 60/548,164, filed Mar. 1, 2004, and 60/479,860 filed Jun. 20, 2003, the contents of each of which are incorporated herein by reference in their entireties.

FIELD OF THE INVENTION

This invention relates generally to a method for the delivery of health promoting compounds to mammals and more specifically the invention relates to a method for encapsulating and embedding a bioactive ingredient in mammalian food or feed formulation.

BACKGROUND OF THE INVENTION

Bioactive proteins include EGF (Epidermal Growth Factor), insulin and insulin-like growth factors, insulin-like growth factors' binding proteins, immunoglobulins (e.g. *H. Pylori* antibody) proline-rich polypeptides, lactoferrin, proteases, lactalbumin, interleukin, lysozyme, TGFA (Transforming Growth Factor A) and PDGF (Platelet Derived Growth Factor).

These proteins may have been shown to have a positive effect on one or more of the following health promotion advantages; protein efficiency ratios, weight gain, immune system functionality, proper growth of organs and cells, systemic and local DNA regulation, maintenance of good health, improvement of disease states and the recovery and cure from disease states Most industrial processes, involve manufacturing conditions that are extremely destructive to potential viability of bioactive compounds like functional proteins. These include high temperatures and pressures, low and high pH, exposure to light, desiccation and other similarly hostile manufacturing conditions. In addition, supply chain constraints impose longer shelf life requirements wherein extended storage under adverse conditions, cause loss of biological activity of these proteins. As a result, inclusion of such compounds in commercially produced feeds and foods (e.g. complete animal rations or baby formulas) is difficult.

This is crucial because mammalian neonates, like human infants, as well as many livestock animal neonates, are frequently deprived of their natural mother's milk immediately or shortly after birth and are nourished primarily with milk substitutes and later, after weaning, with semi-solid and solid mixes and pellets.

This typically means that the desired positive health benefits provided by the original natural mother's milk are largely absent from the natural milk substitute products, as well as from the follow-on, post-weaning mixes and pellets used to feed agriculturally important animal infants.

For example, the immunological components of colostrum and follow-on mature milk include IgG, IgM and IgA. These components confer passive immunity to the neonate and protection against infection during the initial period after parturition. It is has been shown that the presence of insulin (and potentially IGF-1, IGF-2 and EGF) in colostrum and follow-on mature milk leads to a faster and improved development of mammalian neonates' gastrointestinal system fed with such natural mother milk, compared with mammalian neonates fed with artificial substitute foods or feed. Further, it has been demonstrated, that the presence of insulin in colostrum and follow-on mature milk, has a positive effect on reducing of the probability that mammalian infants will develop Diabetes Type 1 (Insulin-dependent Diabetes) later in life. However, insulin and insulin-like proteins are substantially sensitive to manufacturing and environmental storage conditions such as light, radiation, low/high temperatures, low/high pressures, gastrointestinal tract digestive compounds and the presence of chemical compounds.

SUMMARY OF THE INVENTION

In one embodiment of the invention a method is provided for encapsulating and embedding a bioactive ingredient in mammalian newborn formulation comprising the steps of (i) mixing the bioactive ingredient with a food grade or feed grade encapsulating material so as to form a liquid blend, (ii) drying of the liquid blend so as to form a dry blend, and (iii) adding the dry blend to the mammalian newborn formulation, thereby being a method for encapsulating and embedding a bioactive ingredient in mammalian newborn formulation.

In another embodiment of the invention a method is provided for encapsulating and embedding a bioactive ingredient in mammalian newborn formulation comprising the steps of (i) mixing the bioactive ingredient with a food grade or feed grade encapsulating material so as to form a liquid blend, (ii) drying of the liquid blend so as to form a dry blend, (iii) coating the dry blend with at least one additional food grade or feed grade layer of encapsulating material, and (iv) adding the dry blend to the mammalian newborn formulation, thereby being a method for encapsulating and embedding a bioactive ingredient in mammalian newborn formulation.

In another embodiment of the invention, a newborn formulation is provided comprising a bioactive ingredient being encapsulated or embedded in a food grade or feed grade encapsulating material.

In one embodiment of the invention, a method is provided for improving the health status, the growth and the development of a mammal comprising the steps of administering to the mammal a newborn formulation comprising a bioactive ingredient being encapsulated or embedded in a food grade or feed grade encapsulating material said compound capable of improving the health, the growth and the development of a mammal.

In another embodiment of the invention, a method of enriching an infant formula or milk substitute is provided, comprising the step of admixing into the infant formula or the milk substitute, a bioactive ingredient being encapsulated or embedded in a food grade or feed grade encapsulating material.

In one embodiment of the invention, a method is provided for encapsulating or embedding a bioactive ingredient in mammalian solid or semi-solid feed formulation comprising; (i) mixing the bioactive ingredient with a food grade or feed grade encapsulating material forming a liquid blend, (ii) drying of the liquid blend forming a dry blend, (iii) coating the dry blend with at least one additional food grade or feed grade layer of encapsulating material, and (iv) adding the dry blend to the mammalian, solid or semi solid, feed formulation.

In another embodiment, a mammalian solid or semi-solid feed formulation is provided, wherein the solid or semi-solid formulation comprises a bioactive ingredient encapsulated or embedded in a food grade or feed grade encapsulating material.

In one embodiment of the invention, a method is provided for improving the health, the growth and the development of a mammal comprising admixing into the mammalian solid or semi-solid feed formulation comprising a bioactive ingredient encapsulated or embedded in a food grade or feed grade encapsulating material In another embodiment of the invention, a method is provided of enriching mammalian solid or semi-solid feed formulation, comprising the step of admixing into the mammalian solid or semisolid feed formulation a bioactive ingredient being encapsulated or embedded in a food grade or feed grade encapsulating material made with the method comprising; (i) mixing the bioactive ingredient with a food grade or feed grade encapsulating material forming a liquid blend, (ii) drying of the liquid blend forming a dry blend, (iii) coating the dry blend with at least one additional food grade or feed grade layer of encapsulating material, and (iv) adding the dry blend to the mammalian, solid or semi solid, feed formulation.

DETAILED DESCRIPTION OF THE INVENTION

In one embodiment of the invention, a method is provided for the encapsulation of a bioactive material in a food grade or feed grade glassy matrix, the method comprising; (i) mixing a homogeneous intimate mixture between at least one bioactive material and at least one wall forming, food grade or feed grade encapsulating material creating a blend, (ii) mixing said blend with an appropriate plasticizer, (iii) rapidly removing said plasticizer while inhibiting crystallization of the wall forming material thereby resulting in encapsulation of the bioactive material in a food grade or feed grade glassy matrix.

In another embodiment of the invention, a method is provided for the encapsulation of a bioactive material, comprising; (i) mixing at least one bioactive material with a molten, at least one wall-forming food grade or feed grade encapsulating material, and (ii) rapidly cooling the molten, at least one wall forming material thereby resulting in encapsulation of the bioactive material in a food-grade or feed-grade glassy matrix.

In the food and pharmaceutical industries, for example, microencapsulation is used to stabilize the core material, to control the timing and rate of the release of the core material and to separate and prevent chemical interaction between reactive or incompatible components of a multicomponent formulation. Thus, microencapsulation makes it possible to protect sensitive food components, to ensure against nutritional value loss and to mask or preserve flavors and aromas. Encapsulation also increases stability of vitamin supplements, for example, which are normally sensitive to UV radiation, light, oxygen, metals, humidity and temperature. Microencapsulation is also utilized in the pharmaceutical industry to protect the lining of the mouth and esophagus from harsh, orally administered drugs which are released in the stomach by the action of stomach acids on the microcapsule coating.

Encapsulation is a process where one or more active ingredients are coated with, or entrapped within, another material or system. Encapsulation of heat sensitive compounds, such as for example nutraceutical components, enzymes or bioactive proteins, into matrixes that are edible, is generally difficult for a number of reasons. Not the least of which is that conventional encapsulation processes, which expose matrix material and encapsulants to high temperatures such as those, encountered in extrusion, causes thermal destruction or loss of biological viability of the encapsulant. Thus, either large overdoses of encapsulant, which would be very expensive and potentially hazardous, would be required, or the encapsulant would not sustain the encapsulation process at all. If the encapsulant can be encapsulated into a matrix under sufficiently low temperatures, the resulting product is a solid, that is characterized as a hard glass-like solid that is capable of being processed further to yield a flowable powder, amenable to further processing. Moreover, although, the temperature at which the particles are consumed, or the eating temperature, is generally lower than 50 degrees Celsius, which is far below the glass transition temperature, T.sub. careful design of the glassy matrix can release the encapsulant under desired conditions of temperature, moisture and pH. They could also be used as dense pellets for a variety of processing applications, where a controlled release of the heat sensitive encapsulant is desired. The physical hardness of the products and their mechanical stability are advantageous for many processing applications.

In one embodiment, plasticizer as used herein means an additional compound capable of increasing the free volume of the liquid encapsulant without affecting the overall cumulative volume of both encapsulated matrix and the plasticizing compound.

In one embodiment of the invention, protected bioactive ingredient is provided, including, but not limited to, proteins for use in dietary formulations.

In another embodiment of the invention, a method of manufacture the protected bioactive ingredient is provided, so as to retain biological activity of these proteins.

The invention may be used to preserve biological activity of bioactive ingredient against any of the following or similarly destructive factors; adverse temperature, pressure, humidity, pH, osmotic concentration, ionic concentration, chemical degradation, presence of metals, surfactants and chelators, radiation (including but not limited to UV, IR, Visible light), enzymatic and microbial degradation. In addition, the present invention may be used to protect bioactive ingredients against physical changes including but not limited to first and second order phase transitions.

In one embodiment of the invention, a protected bioactive ingredient is provided, which comprises at least one protecting layer enveloping a bioactive ingredient present in maternal mammalian milk.

In another embodiment of the present invention, maternal mammalian milk as used herein means colostrums.

In another embodiment of the invention, the protected bioactive ingredient is present in a natural mammalian milk but its concentration is significantly lower, non viable, non available or non-existent in commercially processed milk or milk substitute.

In another embodiment of the present invention, concentration as used herein means Molar concentration and its fractions, or percentage relative to that existing in colostrums.

As used herein, the term "significantly lower" in one embodiment means that the amount of the bioactive ingredient in commercially processed milk is between about 0.1 to about 50 percent of that present in colostrum.

In one embodiment of the invention, the amount of the bioactive ingredient in commercially processed milk is at the most, 50 percent of that present in colostrum.

In another embodiment of the invention, the amount of the bioactive ingredient in commercially processed milk is at the most, 25 percent of that present in colostrum.

In another embodiment of the invention, the amount of the bioactive ingredient in commercially processed milk is at the most 10 percent of that present in colostrum.

In another embodiment of the invention, the amount of the bioactive ingredient in commercially processed milk is at the most 1 percent of that present in colostrum.

In another embodiment of the invention, the amount of the bioactive ingredient in commercially processed milk is at the most 0.1 percent of that present in colostrum.

In another embodiment, the amount in the processed milk is not detectable by the means known to one skilled in the art.

In one embodiment of the invention, at least a single protecting layer enable the maintenance of the bioactive properties of the bioactive ingredient while in a "dormant state", which is, in one embodiment of the invention, when the protected protein is in dry or materially dry conditions, such as those present in powdered infant formulas, milk substitute products, and semi-solid/solid mixes and pellets.

In another embodiment, dormant state of the protein as used herein means the preservation of the native tertiary and quarternary structures of the protein in an anhydrous state.

In one embodiment of the invention the at least one single protecting layer provides protection to the encapsulated bioactive ingredient, so that the protein shall materially maintain its bioactive properties in hostile conditions such as high temperatures normally leading to proteins' denaturation, high pressures, humidity, adverse osmotic pressures, high or low pH, strong enzymatic degradation, high solvent concentration and the like. Then, in another embodiment, based on the triggering event, the outer protection layer is dissolved, and the "dormant" bioactive ingredient will be released and become physiologically active.

In one embodiment, the protected bioactive ingredient is designed in a way whereby the release of the bioactive ingredient occurs before entering the GI system of the newborn mammal consuming the formulation.

In another embodiment of the invention, the release may be while in contact with the different parts of the gastrointestinal tract.

In one embodiment of the present invention, the encapsulated bioactive ingredient will be protected from conditions encountered during commercial extrusion process, including but not limited to cold extrusion or hot extrusion either at standard temperatures and pressures or at conditions different than standard temperatures and pressures.

In another embodiment of the present invention, the encapsulated bioactive ingredient will be protected from conditions encountered during commercial size reduction processes, including but not limited to colloid mills, both stator rotor of the frusto conical type, as well as cron and tooth type, ball mills, impact mills, jet impingement mills, homogenizing mills, sonication, high velocity mixers and membrane emulsification devices.

In one embodiment of the present invention, the encapsulated bioactive ingredient will be protected from conditions encountered during commercial baking processes.

In another embodiment, the protected bioactive ingredient will be protected from conditions encountered during commercial freezing processes.

In one embodiment of the invention, a newborn formulation is provided, comprising a bioactive ingredient being encapsulated or embedded in an edible ingredient.

In one embodiment of the invention, the newborn formulation may be an infant formula or a milk replacer/substitute for mammal's newborn consumption.

In another embodiment, the milk replacer/substitute as used herein is any milk replacer/substitute for mammalian neonates wherein the mammals are of the bovine, equine, and swine families for examples calf, lamb, pig, cows, sheep, goat, yaez, cats, dogs and horses.

In one embodiment of the invention, the milk replacer/substitute is any milk replacer/substitute for mammalian neonates wherein the mammals are of the feline and canine families.

In another embodiment the bioactive ingredient is encapsulated in a plasticizable matrix material, which is plasticizable at low temperatures by a liquid plasticizer or by liquid encapsulant component, which may be a plasticizable biopolymer.

In one embodiment, the plasticized material includes but is not limited to a carbohydrate polysaccharides, such as pentosans, a physically or chemically modified starch or cyclodextrin and mixtures thereof.

In another embodiment, the plasticized material is a polymer such as polyvinylpyrrolidone (PVP, Povidone) or other non-hydrophobic polymers such as N-vinylpyrrolidone (NVP) and (vinyl)acetate copolymers, (polyvinyl)alcohol chitosan or mixtures thereof. In one embodiment, the plasticized material is cellulose esters, cellulose ethers, and polyethylene glycol. In another embodiment, the plasticized material is a hydrocolloid such as xanthan, carragenan, alginate, gum arabic, gum acacia, gum tragacanth, gum conjac and mixtures thereof.

In one embodiment, the plasticized material is glutenins and gliadins, such as vital wheat gluten or isolated gluten, zein, vegetable or dairy proteins such as protein from soy or milk, and mixtures thereof.

In another embodiment of the present invention, starches that may be used in the present invention are physically or chemically modified starches, with amylose/amylopectin ratios of between about 1 to about 0.001, derived from corn, wheat, rice, potato, tapioca, yuka and arrow root.

In one embodiment, sources of starch which may be used also include flours from grains such as corn, wheat, durum wheat, rice, barley, oat, or rye, and mixtures thereof.

In another embodiment, since the microcapsules formed are to be used in a newborn formula or in a solid or semi-solid feed formulation, only wall material approved by the FDA or similar regulatory body in Europe and elsewhere shall be used.

In one embodiment the GRAS list provides a listing of compounds that can be used for forming the capsule walls.

In one embodiment of the present invention, any other food-grade or feed-grade encapsulating material, which has been approved by a recognized regulatory body for human and/or animal consumption (as applicable), shall serve as the encapsulation material in the process.

In one embodiment of the present invention, the wall material used is poly (DL-lactide-co-glycolide).

In another embodiment of the invention the food grade or feed-grade encapsulating material, used in the neonate formulation comprises, polysaccharide, maltodextrin, milk powder, whey protein, lipid, gum Arabic or microcrystalline cellulose or combinations thereof.

In one embodiment of the invention the bioactive ingredient being encapsulated or embedded maintains or substantially maintains its biologically bioactive function and properties during the process of formulating the newborn formulation.

In one embodiment of the invention the bioactive ingredient being encapsulated or embedded maintains or substantially maintains its biologically bioactive function and properties during the normal shelf-life of the underlying newborn formulation or solid or semi-solid feed formulation in which it is incorporated.

In one embodiment of the invention the bioactive ingredient may be a glycoprotein, immunoglobulin, peptide, polypeptide, hormone or enzyme.

In another embodiment of the invention, the bioactive ingredient is insulin, IGF-I, IGF-2, or EGF.

In one embodiment of the invention the bioactive ingredients include but is by no way limited to alpha-1-proteinase inhibitor, alkaline phosphatase, angiogenin, antithrombin III, chitinase, extracellular superoxide dismutase, Factor VIII, Factor IX, Factor X, fibrinogen, glucocerebrosidase, glutamate decarboxylase, human serum albumin, myelin basic protein, lactoferrin, lactoglobulin, lysozyme, lactalbumin, proinsulin, soluble CD4, component and complexes of soluble CD4, tissue plasminogen activator and a variant thereof combinations thereof and pharmaceutically acceptable salts thereof.

In another embodiment of the present invention, the insulin or any other proteins may be recombinant, synthetic, purified from natural source, biologically active and a peptide or polypeptide having an amino acid sequence of human or mammalian protein (e.g., human or bovine or porcine insulin).

In one embodiment, crude extracts may be useful, depending on the method of their manufacture, for example synthetic protein may be manufactured using chemical peptide synthesis or any other similarly suitable method.

In one embodiment of the invention the newborn formulation comprises uniformly sized particles of encapsulated bioactive ingredient, wherein the particles have a radius between about 0.001 and about 5,000 micrometers.

In one embodiment of the present invention, solid feed formulation as used herein means a formulation able to maintain its density at room temperature and support its own weight.

In another embodiment of the invention, semi-solid formulation as used herein means formulations capable of flowing under their own weight, with viscosities between about 1 to about 600,000 Pascal seconds.

In one embodiment of the present invention, the formulation is being used for post weaning mammals.

In another embodiment, post-weaning mammals as used herein refers to the age at which the intensively grown mammals are typically weaned off the mother's milk. For example, intensively grown lambs are typically weaned between 25-35 days from birth. Intensively grown piglets are typically weaned between 30-50 days from birth; Intestively-grown calves are typically weaned between 40-70 days from birth.

In all of these newborn animals, in one embodiment of the invention, the provided quantity of the milk replacer containing the bioactive ingredient is gradually reduced, and the quantity of the mix, pellets or other semi-solid or solid feed is increased.

According to another embodiment of the present invention, the integration of a bioactive ingredient in mix/pellets was advantageous for as long as 1-9 months post-weaning.

In one embodiment of the invention, the solid or semi-solid feed formulation may be in the form including but not limited to a mash, pellets, granules, agglomerate, extrudate or combinations thereof.

In another embodiment of the invention, the bioactive ingredient being encapsulated or embedded maintains or substantially maintains its biological function during the process of formulating the mammalian solid or semi-solid feed formulation.

In another embodiment of the invention, the bioactive ingredient being encapsulated or embedded maintains or substantially maintains its biological function during the digestion of the feed.

In one embodiment of the invention, the bioactive ingredient being encapsulated or embedded is released upon contact with a liquid.

In one embodiment of the invention, the solid or semi-solid feed formulation is protein glycoprotein, immunoglobulin, peptide, polypeptide, hormone or enzyme, either alone or in combination.

In another embodiment of the invention, the bioactive ingredient may be insulin, IGF-I, IGF-II or EGF, either alone or in combination.

In one embodiment of the invention, the bioactive ingredient is being encapsulated or embedded in a polysaccharide, such as maltodextrin.

In another embodiment of the invention, the mammalian solid or semi-solid feed formulation comprises uniformly sized particles of encapsulated bioactive ingredient, wherein the particles have an average size of between about 10 to about 4000 micrometers.

The formulations used in one embodiment of the invention are efficient for increasing the rate of weight gain of mammals, preventing diarrhea and other gastric disorders and are useful for increasing the life expectancy of mammals after birth.

Products containing protected bioactive ingredients according to another embodiment of the present invention may be consumed by a variety of subjects, including, but not limited to, preterm infants, post-discharge preterm infants, term infants, babies, toddlers, children, adolescents, adults, elderly humans, the infants or adults of mammalian non-human animals, including but not limited to bovine, porcine, caprine, feline, canine or equine species as well as infants or adults of non-mammalian animals.

In another embodiment of the invention a method for encapsulating and embedding a bioactive ingredient in mammalian newborn formulation is provided, comprising the steps of, (i) mixing the bioactive ingredient with an edible food grade or feed grade encapsulating material forming a liquid blend; (ii) drying of the liquid blend; (iii) coating the dry blend with at least one additional food grade or feed grade encapsulating material layer; and (iv) adding the dry blend to the mammalian newborn formulation.

In one embodiment the mammalian newborn food formulation may be infant formula or milk replacer/substitute. Such a formulation is in another embodiment, a form of powder, a solution, a suspension, an emulsion, an ointment, a cream in both liquid, semi-solid or a solid form In another embodiment of the invention, a formulation for post weaning mammals which is a solid or a semi-solid formulation is provided, comprising an encapsulated and embedded bioactive ingredient prepared by the following process: (i) mixing the bioactive ingredient with a food grade or feed grade encapsulating material so as to form a liquid blend; (ii) drying of the liquid blend so as to form a dry blend; (iii) coating the dry blend with at least one additional food grade or feed grade encapsulating material layer; and (iv) adding the dry blend to the mammalian solid or semi-solid feed formulation. The solid or semi-solid formulation may be in a form of pellets or mash/mix.

Further, according to one embodiment of the present invention, the step of mixing the bioactive material and the wall forming food grade or feed grade material, involves the addition of liquid, such as, but not limited to: water, saline, alcohol, molasses, or similar food grade or feed grade encapsulating material solvent.

In another embodiment of the present invention, the ratio between the food grade or feed grade material and the solvent of the food grade or feed grade encapsulating material may be in one embodiment of the invention between about 1:1 to about 1:1000.

In one embodiments of the invention the ratio between the food grade or feed grade material and the solvent of the food grade or feed grade encapsulating material is between 1:3 and 1:100.

In another embodiment of the invention, the dry blend is ground further.

The encapsulated bioactive ingredient in one embodiment may be further encapsulated by at least one additional protection layer, which may be formed in another embodiment of the same food grade or feed grade encapsulating material or, in another embodiment a different food or feed grade encapsulating material.

In one embodiment the dry blend is further mixed with said food or feed grade encapsulating material so as to form at least one other layer of food grade or feed grade encapsulating material layer enveloping the bioactive ingredient.

In one embodiment of the invention the bioactive ingredient may be alpha-1 proteinase inhibitor, alkaline phosphatase, angiogenin, antithrombin III, chitinase, extracellular superoxide dismutase, Factor VIII, Factor IX, Factor X, fibrinogen, glucocerebrosidase, glutamate decarboxylase, human serum albumin, myelin basic protein, lactoferrin, lactoglobulin, lysozyme, lactalbumin, proinsulin, soluble CD4, component and complexes of soluble CD4, tissue plasminogen activator or variant, pharmaceutically acceptable salt or combination thereof.

In another embodiment of the invention, the food grade or feed grade encapsulating material is a polysaccharide, milk powder, whey protein, lipid, gum Arabic microcrystalline cellulose, their analogs or combinations thereof.

In one embodiment of the invention the food grade or feed grade encapsulating material, is a solid at temperatures of up to 70° C.

In another embodiment of the invention, the step of drying the food grade or feed grade encapsulating material and the bioactive material is done using the methods including but not limited to; freeze drying, vacuum drying, spray drying, osmotic dehydration, fluidized bed dehydration, solvent evaporation dehydration, sonication assisted dehydration, microwave-assisted dehydration, RF-assisted dehydration, either alone or commercially acceptable combinations thereof.

In one embodiment of the invention, the liquid mix is lyophilized after incorporating at least one bioactive ingredient and at least one food or feed grade encapsulating material ingredient.

In one embodiment lyophilization produces droplets containing at least one protected bioactive ingredient and at least one food grade or feed grade encapsulating material in a glassy state.

In one embodiment, a flash freezer is employed to dry the liquid mix through the utilization of liquid gas, including, but not limited to, nitrogen, $CO_2$, etc.

In one embodiment, the size of the droplets will vary between about 10 and about 5,000 micrometers.

In another embodiment the droplets size distribution depends on a variety of parameters including but not limited to, freeze sprayer nozzle size, liquid gas temperature, chamber temperature, mix components ratio, mix and gas flow-rates, encapsulating food grade or feed grade material concentration, plasticizer type and amount and freeze chamber wall geometry.

In one embodiment of the invention, the size distribution of the glassy droplets resulting from the process ranges between 50 microns and 1,000 microns.

In one embodiment this treatment results in glassy frozen micro droplets, where each micro droplet contains at least one protected bioactive ingredient, at least one food grade or feed grade encapsulating material and the food grade or feed grade solvent.

In another embodiment once such frozen droplets are placed in temperatures above the melting temperature of the mix, the liquid mix from the previous phase of the process shall be reconstituted.

In one embodiment of the invention, the process further includes the freeze-drying of a combination of at least one bioactive ingredient and at least one food grade or feed grade encapsulating material.

In another embodiment, freeze drying may be carried out on either a liquid mixture of at least one protected bioactive ingredient and at least one food grade or feed grade encapsulating material or on frozen glassy micro droplets as described hereinabove.

In one embodiment the result of this freeze drying process is dry glassy material which includes at least one food grade or feed grade encapsulating material and the at least one protected bioactive ingredient.

In another embodiment, freeze drying was performed on a liquid mixture, the result of the process was bulk dry material, porous by nature, containing a glassy matrix of the dried food-grade or feed grade encapsulating material encapsulating the bioactive ingredient.

In one embodiment, freeze-drying was performed on the output of the flash freeze spraying process, resulting in glassy droplets, with the food grade or feed grade encapsulating material incorporating the bioactive ingredient.

In another embodiment, low-temperature spray drying of combination of at least one bioactive ingredient and at least one food grade or feed grade encapsulating material was carried out.

In one embodiment, the bioactive material was dispersed in the food grade or feed grade encapsulating material and atomized at a maximum temperature of 45° C.

In another embodiment, the maximum temperature is 37° C., preventing denaturation of the bioactive ingredient. In one embodiment, spray drying may be carried out on a liquid mixture of at least one protected bioactive ingredient, at least one food grade or feed grade encapsulating material and at least one chaperon-like protecting protein, resulting in dry material which comprises the food grade or feed grade encapsulating material and the at least one protected bioactive ingredient.

In one embodiment of the invention, the dehydration of the food grade or feed grade encapsulating material and the bioactive material conducted at a temperature, which is preferably below the denaturation temperature of the bioactive ingredient, when that bioactive ingredient is protein.

In another embodiment, the dehydration of the food grade or feed grade encapsulating material and the bioactive material is carried out at temperature below the onset temperature for the bioactive materials' degradation threshold.

In one embodiment of the invention, the dehydration process of food grade or feed grade encapsulating material and the bioactive material is carried out at a maximum temperature of 50° C.

In another embodiment of the invention, the step of drying the liquid blend results in glassy freeze-dried droplets containing a bioactive ingredient and at least one food grade or feed grade encapsulating material.

In one embodiment of the invention the step of freeze-drying is preceded by a step of spraying the liquid blend through an atomizer in the presence of a liquid gas.

In one embodiment, extrusion is used as an encapsulation method in which a core material is dispersed in a liquid mass of a bioactive ingredient and at least one food grade or feed grade encapsulating material and ultimately formed into microcapsule.

In another embodiment of the invention, encapsulating or embedding the bioactive ingredient in the formulation described above involves an additional step of premixing the blend in a small volume of the mammalian newborn formulation or food grade or feed grade encapsulating material, or semi solid or solid formulation, to ensure homogeneity prior to its mixing with the whole formulation.

In one embodiment of the invention, protection processes suited for use as used herein include, but are not limited to those which produce a protected bioactive ingredient in the form of a: powder, a micro-encapsulated powder, a nano-encapsulated powder, a liquid, a micro-emulsified liquid, a nano-emulsified liquid, a solution, a micro-emulsified solution, a nano-emulsified solution, a spread, a mash, an ointment, micro droplets, nano-droplets, tablets and solids such as for example, pellets.

In another embodiment of the invention, the encapsulation process includes duplex, W/O/W, O/W/O, double or multiple emulsions.

In one embodiment of the invention, the mix of at least one bioactive material and at least one food grade or feed grade encapsulating material and at least one surfactant selected from the group of surfactants having an HLB value substantially below 7 are suspended in a non-miscible, food grade or feed grade material and further mixed affecting size reduction using methods hereinabove mentioned.

In another embodiment, the milled emulsion is further mixed with a food grade or feed grade material that is miscible with the food-grade or feed grade encapsulating material and a food grade or feed grade surfactant selected from the group of surfactants having an HLB value substantially higher than 7 and further reduced in size using one of the methods hereinabove mentioned.

According to an embodiment of the invention, following formulation of a bioactive ingredient, micro emulsification or nano emulsification of the bioactive ingredients is conducted.

In one embodiment, the formulated bioactive ingredient is mixed with an emulsion incorporating water, oil phase and surfactant. As a result of such mixing, the bioactive ingredient's molecules are reorganized into the dispersed phase of the emulsion.

The protection provided to the bioactive ingredients by the micro or nano emulsion in another embodiment, relates to temperature exposure protection, and improved solubility of the bioactive ingredients within the food or feed with which it is integrated, following the release of the bioactive ingredients from its encapsulation prior to its consumption and/or during the digestion process.

In another embodiment, the bioactive ingredient in the nano emulsion or micro emulsion is initially protected within the liquid micro emulsion or liquid nano emulsion.

A person holding ordinary skill in the art would readily recognize that this invention is not limited in its application to the details of construction and the arrangement of components set forth in the hereinbelow mentioned description. It should be appreciated that various modifications can be made without materially changing the scope or spirit of the current invention. It should be noted that practicing the invention is not limited to the to the applications hereinbelow mentioned and many other applications and alterations may be made without departing from the intended scope of the present invention Also, it is to be understood that the lexicography employed herein is for the purpose of description and should not be taken as limiting.

In one embodiment of the invention, a method is provided for the encapsulation of a bioactive material in a food grade glassy matrix, the method comprising; (i) mixing a homogeneous intimate mixture between at least one bioactive material and at least one wall forming, food grade or feed grade encapsulating material creating a blend, (ii) mixing said blend with an appropriate plasticizer, (iii) rapidly removing said plasticizer while inhibiting crystallization of the wall forming material thereby resulting in encapsulation of the bioactive material in a food grade or feed grade glassy matrix.

In another embodiment of the invention, a method is provided for the encapsulation of a bioactive material, comprising; (i) mixing at least one bioactive material with a molten, at least one wall-forming food grade or feed grade encapsulating material, and (ii) rapidly cooling the molten, at least one wall forming material thereby resulting in encapsulation of the bioactive material in a food-grade or feed-grade glassy matrix.

In another embodiment of the invention, a method for encapsulating and embedding a bioactive ingredient in mammalian newborn formulation is provided, the method comprising; (i) mixing the bioactive ingredient with a food grade or feed grade encapsulating material so as to form a liquid blend, (ii) drying of the liquid blend so as to form a dry blend; (iii) coating the dry blend with at least one additional food grade or feed grade encapsulating material layer, and (iv) adding the dry blend to the mammalian newborn formulation thereby being a method for encapsulating and embedding a bioactive ingredient in mammalian newborn formulation.

In one embodiment of the invention, a mammalian newborn formulation is provided comprising a bioactive ingredient being encapsulated or embedded in a food grade or feed grade encapsulating material.

In another embodiment of the invention, a method for encapsulating or embedding a bioactive ingredient in mammalian solid or semi solid feed formulation is provided, comprising the steps of; (i) mixing the bioactive ingredient with a food grade or feed grade encapsulating material so as to form a liquid blend, (ii) drying of the liquid blend so as to form a dry blend, (iii) coating the dry blend with at least one additional food grade or feed grade encapsulating material layer, and (iv) adding the dry blend to the mammalian solid or semi solid feed formulation thereby being a method for encapsulating and embedding a bioactive ingredient in mammalian solid or semi solid feed formulation.

In another embodiment of the invention, a mammalian solid or semi-solid feed formulation is provided, comprising a bioactive ingredient being encapsulated or embedded in a food grade or feed grade material The following examples are presented in order to more fully illustrate some embodiments of the invention. They should, in no way be construed, however, as limiting the scope of the invention.

EXAMPLES

Example 1

Effects of Dietary Insulin on Weight Gain in Bovine Neonates

Materials and Methods

100 Friesy and Charole' calves in ages 12-15 days from birth, were used. Each calf received a milk replacer, of up to 6 litters a day, until the 37th day from birth. From the 37th day, milk replacer quantity was reduced by 0.5 litters every 2 days while simultaneously, pellets quantity increased, until the calf's 57th days old, when it is considered fully weaned. Calves in the experimental group receive 600 MicroUnits/cc. of liquid milk replacer. Calves in the control group receive no insulin at all. Daily growth in grams per each 1 Kg. of birth weight was measured and calculated for each calf.

Results

The insulin treated group gained up to 26% more weight comparing with the control group during the period of between days 17 and day 67 after birth. At the end of the study period, the average daily weight growth in grams per each Kg. of birth weight was 22.47, compared to 18.71 g/Kg birth weight in the control group at the same time period. These results confirm that insulin is an important factors contributing to the weight gain in calves at the age of between 12-15 days and 68 days from birth.

Example 2

Effects of Feed formula Enriched with Encapsulated Bioactive Ingredient on Caprine Neonates' Health Status Materials and Methods More than 1,000 Assaf specie lambs over a period of 12 months at the age of 2-3 days from birth, were used. The growing period was divided into two periods: 3-28 days from birth, during which the lambs were exclusively fed by a milk replacer; and 29-75 days from birth, during which the lambs were fed by post-weaning mix/mash. Lambs in the study groups received between 600 MicroUnits-3,000 MicroUnits of insulin/ml. of milk replacer, and between 1,600 MicroUnits-5,000 MicroUnits of insulin/gr. of mix/mash. The lambs in the control groups did not receive insulin at all.

A liquid blend, of 4 Kilograms of Maltodextrin, 40 Liters of Saline 0.9% and 100,000 IU (International Units) of insulin was blended (e.g., 25 IU insulin per 1 g of Maltodextrin). The liquid blend was then freeze-dried. The product of the process was maltodextrin encapsulated insulin. 97% of the bioactive properties of the insulin were maintained after the freeze-drying process. A premix of 10 Kg. was prepared from standard milk powder and the maltodextrin encapsulated insulin. The premix was then blended with 740 Kg. of standard milk replacer product, to generate 750 Kg. of insulin enriched commercial milk replacer.

Results

Weight Gain:

On average, lambs in the study groups which received insulin both in the milk replacer and the mix/mash, gained between 5% to 7% more weight in comparison to the control groups. Lambs in the study groups receiving insulin only in the milk replacer (but not in the mix/mash), gained between 3% to 5% more weight in comparison to the control groups.

Disease Incidence:

The lambs in the study groups suffered between 10%-25% fewer incidents of Diarrhea and/or Pneumonia, comparing with lambs in the control groups. Further, recovery of lambs suffering such disease states was between 5%-20% quicker in comparison with the lambs in the control groups.

Death Rate:

The death rate in the study groups was between 20% and 80% lower in comparison with control groups, depending on the specific study. For example, in one study, the insulin fed group started the study with 70 newly born lambs, and at marketing (e.g. 150 days after birth) 68 lambs survived. (2.8% death rate). In the control group, receiving no insulin, the group started with 69 newborn lambs, and at marketing, only 61 lambs survived (e.g. 11.6% death rate). This means that the death rate in the insulin-fed group was lower by 74.8% comparing with the control group.

These results confirm that insulin is an important factor contributing to the weight gain and health in lambs between the ages of 2-3 days and 75 days from birth. Furthermore, the result show that encapsulated insulin maintains biological activity of insulin during the preparation process of the solid feed and during the transfer in the lamb's digestion system.

What is claimed is:

1. A method for encapsulating or embedding a heat sensitive bioactive ingredient in a mammalian newborn food or feed formulation, comprising:
   (i) mixing insulin, maltodextrin and a liquid to form a liquid blend;
   (ii) drying the liquid blend of step (i) to form a dry blend;
   (iii) coating the dried blend of step (ii) with an encapsulating layer comprising maltodextrin;
   (iv) adding the coated dry blend of step (iii) to a mammalian newborn food or feed formulation, wherein the steps of mixing and drying are conducted at a maximum temperature of 50° C., such that the activity of the heat sensitive bioactive ingredient is substantially maintained.

2. The method of claim 1, wherein the liquid blend of step (i) further comprises saline.

3. The method of claim 1, wherein the insulin is recombinant human insulin.

4. The method of claim 1, further comprising reducing the particle size of the encapsulated or embedded bioactive ingredient.

5. The method of claim 1, wherein the method provides uniformly sized particles of an encapsulated or embedded bioactive ingredient, having an average size of between about 50 to about 1000 micrometers.

6. The method of claim 1, wherein the mammalian newborn food or feed formulation is an infant formula, a milk replacer, or a milk substitute.

7. The method of claim 1, wherein the mammalian newborn food or feed formulation is in the form of a powder, a solution, a suspension, an emulsion, an ointment, or a cream.

8. The method of claim 1, wherein the maximum temperature is 37° C.

9. A mammalian newborn food or feed formulation comprising an encapsulated or embedded heat sensitive bioactive ingredient prepared by the method of claim 1.

10. A mammalian newborn food or feed formulation comprising an encapsulated or embedded heat sensitive bioactive ingredient prepared by the method of claim 2.

11. A mammalian newborn food or feed formulation comprising an encapsulated or embedded heat sensitive bioactive ingredient prepared by the method of claim 3.

12. A mammalian newborn food or feed formulation comprising an encapsulated or embedded heat sensitive bioactive ingredient prepared by the method of claim 4.

13. A mammalian newborn food or feed formulation comprising an encapsulated or embedded heat sensitive bioactive ingredient prepared by the method of claim 5.

14. A mammalian newborn food or feed formulation comprising an encapsulated or embedded heat sensitive bioactive ingredient prepared by the method of claim 6.

15. A mammalian newborn food or feed formulation comprising an encapsulated or embedded heat sensitive bioactive ingredient prepared by the method of claim 7.

16. A mammalian newborn food or feed formulation comprising an encapsulated or embedded heat sensitive bioactive ingredient prepared by the method of claim 8.

\* \* \* \* \*